(12) United States Patent
Roberge et al.

(10) Patent No.: US 7,939,698 B2
(45) Date of Patent: May 10, 2011

(54) METHOD FOR GRIGNARD TYPE REACTIONS IN MICROREACTORS

(75) Inventors: Dominique Roberge, Sierre (CH); Nikolaus Bieler, Brig-Glis (CH); Laurent Ducry, Sierre (CH)

(73) Assignee: Lonza AG, Basel (CH)

( * ) Notice: Subject to any disclaimer, the term of this patent is extended or adjusted under 35 U.S.C. 154(b) by 218 days.

(21) Appl. No.: 12/373,636

(22) PCT Filed: Jul. 11, 2007

(86) PCT No.: PCT/EP2007/006127
§ 371 (c)(1),
(2), (4) Date: Jan. 13, 2009

(87) PCT Pub. No.: WO2008/009378
PCT Pub. Date: Jan. 24, 2008

(65) Prior Publication Data
US 2009/0270663 A1    Oct. 29, 2009

Related U.S. Application Data

(60) Provisional application No. 60/831,922, filed on Jul. 20, 2006.

(30) Foreign Application Priority Data

Jul. 18, 2006  (EP) .................................... 06014883

(51) Int. Cl.
*C07C 17/38* (2006.01)
(52) U.S. Cl. ...................................... 570/262; 422/102
(58) Field of Classification Search .................... None
See application file for complete search history.

(56) References Cited

U.S. PATENT DOCUMENTS

| | | | |
|---|---|---|---|
| 7,098,344 B2 * | 8/2006 | Koop et al. ............... | 548/303.7 |
| 2003/0175168 A1 * | 9/2003 | Gilligan et al. ............ | 422/102 |
| 2005/0072686 A1 * | 4/2005 | Shaw et al. ............... | 205/334 |

FOREIGN PATENT DOCUMENTS

| WO | WO 01/51434 A1 | 7/2001 |
|---|---|---|
| WO | WO 02/083988 A2 | 10/2002 |

* cited by examiner

*Primary Examiner* — Sudhakar Katakam
(74) *Attorney, Agent, or Firm* — Hoffmann & Baron, LLP

(57) ABSTRACT

The present invention relates to a process for Grignard type reactions comprising mixing at least two fluids in a microreactor having at least two injection points.

21 Claims, 1 Drawing Sheet

METHOD FOR GRIGNARD TYPE REACTIONS IN MICROREACTORS

This application is the U.S. National Phase of, and Applicants claim priority from, International Application Number PCT/EP2007/006127 filed 11 Jul. 2007, European Patent Application bearing Serial No. 06014883.0 and U.S. Patent Application bearing Ser. No. 60/831,922, which are incorporated herein by reference.

BACKGROUND OF THE INVENTION

The present invention relates to a process for Grignard type reactions comprising mixing at least two fluids in a microreactor.

Grignard type reactions are very important reactions in preparative chemistry. In general, a Grignard type reaction is the reaction of compounds of formula

or

wherein $R^1$ is selected from the group consisting of alkyl, cycloalkyl, alkenyl, alkynyl, aryl and aralkyl, and wherein X is a halogen atom selected from the group consisting of chlorine, bromine and iodine, with a compound of formula

wherein $R^2$ is alkyl, cycloalkyl, alkenyl, alkynyl, aryl and aralkyl, and X is halogen; or with a compound containing a polar multiple bond like C=O, C=N, C≡N, C=S, N=O and S=O. The compound of formula I is called the Grignard reagent. Other uses of the compounds of formulae I or II are the exchange of halogen atoms of boron, silica, tin or antimony compounds or the preparation of highly reactive Grignard compounds which are otherwise hard to obtain.

Performing Grignard reactions using single micro mixers is disclosed in EP-A-1285924. The disclosed method is not applicable to industrial scale productions.

A persistent aim of the chemical industry is to constantly improve and control chemical reactions. Greater control over reactions may lead to, for example, improvements in safety, increase in reaction product yield and/or purity, or the isolation of valuable highly reactive intermediate products. In particular, greater control over reagent mixing, fluid flow, heat sinking/sourcing and catalytic efficiency is desirable.

A general method which provides such improved control over reactions would therefore be advantageous. Particularly, methods for performing exothermic reactions in large scale in a controlled manner are sought-for.

SUMMARY OF THE INVENTION

According to the present invention there is provided a method for carrying out a Grignard reaction comprising mixing at least two fluids, one of the at least two fluids comprising a compound able to react with a Grignard reagent in a Grignard type reaction (1$^{st}$ reactant) and another fluid comprising a Grignard reagent (2$^{nd}$ reactant), and optionally further fluids, said mixing taking place in a microreactor (6) comprising at least one flow path (1) for one of the at least two fluids (A) comprising either the 1$^{st}$ or 2$^{nd}$ reactant, said flow path(s) comprising at least two reaction regions (2), each reaction region comprising an injection point (3) for feeding the other one of the at least two fluids (B) comprising either the 2$^{nd}$ or the 1$^{st}$ reactant, a mixing zone (4) in which the at least two fluids contact each other and a reaction zone (5), and wherein the microreactor optionally provides one or more additional residence time volumes, and wherein in said method one of the at least two fluids comprising either the 1$^{st}$ or 2$^{nd}$ reactant establishes a first flow and wherein the other one of the at least two fluids comprising either the 2$^{nd}$ or 1$^{st}$ reactant is injected into said first flow at least at two injection points (3) along said flow path(s) (1) in a way such that at each injection point only a fraction of the amount necessary to reach completion of the Grignard type reaction is injected.

Usually the expression "microreactor" is used for a reactor which reaction volumes have dimensions (perpendicular to the flow direction) of about 10000 micrometers and less.

The expression "necessary to reach completion of the reaction" means the amount which would have to be added to reach "theoretical" completion of the reaction for example in a single vessel. In a simple 1:1 reaction stoichiometry this would be equimolar amounts. For a 1$^{st}$ reactant like $BCl_3$ as in reaction (xvi) below depending on the desired product one, two or three molar equivalents of a Grignard reagent bearing one —MgX group are necessary to complete the reaction. In the case where the Grignard reagent comprises two —MgX groups as in reaction (xviii) below two molar equivalents of the 1$^{st}$ reactant are necessary for completion.

BRIEF DESCRIPTION OF THE DRAWINGS

The preferred embodiments of the method for Grignard type reactions in microreactors of the present invention, as well as other objects, features and advantages of this invention, will be apparent from the accompanying drawings wherein.

DETAILED DESCRIPTION OF THE INVENTION

Figure 1:
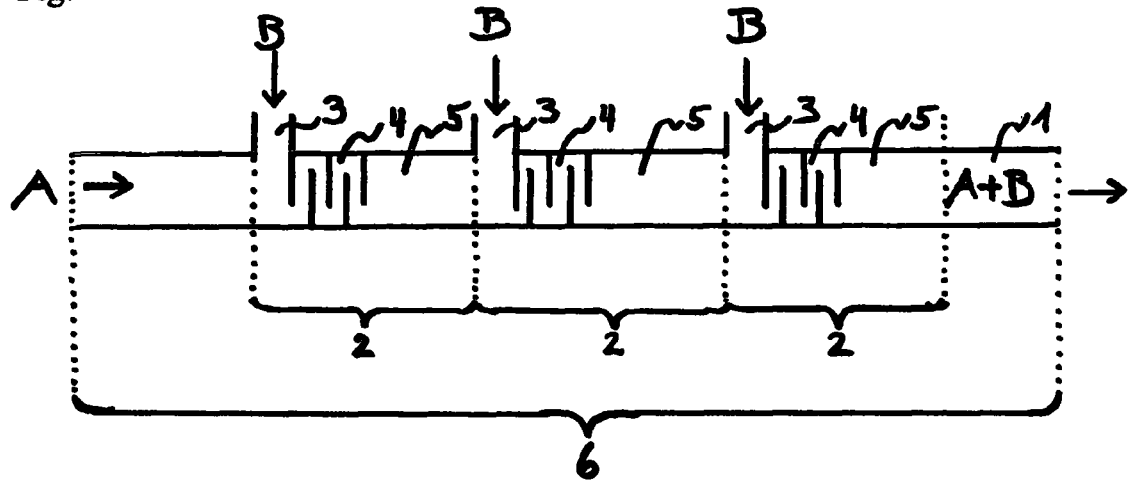
FIG. 1 illustrates a first embodiment of the microreactor of the present invention and shows one flow path with three injection points.

The most important use of magnesium in preparative organic chemistry is the reductive formation of Grignard compounds from organic halides with umpolung of the halogen-bearing carbon atom. In magnesium organic compounds or Grignard compounds the carbon-magnesium bond is strongly polarized and the carbon atom attached to magnesium carries a negative charge. Suitable Grignard reagents for reaction in the inventive method are compounds of formula

or

wherein $R^1$ is selected from the group consisting of alkyl, cycloalkyl, alkenyl, alkynyl, aryl and aralkyl, and wherein X is a halogen atom selected from the group consisting of chlorine, bromine and iodine. In a preferred embodiment a Grignard compound of formula I is used. Under suitable conditions Grignard compounds can be stored as such. Compounds of formula I and II exist in Schlenk equilibrium. Depending on the substituents the equilibrium in shifted more to one side. Both compounds may be used equivalently although compounds of formula II generally react slower than compounds of formula I.

In a preferred embodiment the Grignard reagent may contain two or more —MgX groups, being connected through an linear, branched or carbocyclic group. Accordingly, here and hereinbelow compounds of formula I may also represent for example compounds of formulae

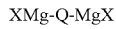    (Ia), or

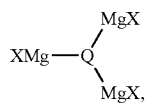    (Ib)

and the like wherein Q is selected from the group consisting of di- or trivalent hydrocarbon moieties, such as cycloalkanes, alkenyl, alkynyl aryl and aralkyl as defined above wherein one, two or more hydrogen atoms are replaced with the respective number of —MgX groups.

Each of the above mentioned radicals may optionally carry further functional groups not being able to react with the Grignard compound under Grignard type reaction conditions.

Among others compounds of formula

    (III), wherein $R^2$ is selected from the group consisting of alkyl, cycloalkyl, alkenyl, alkynyl, aryl and aralkyl, and X is halogen
as well as compounds comprising one or more polar multiple bonds like C=O, C=N, C≡N, C=S, N=O and S=O or compounds having at least one activated hydrogen atom are able to react with Grignard reagents in a Grignard type reaction and can be used according to the method of the present invention.

Compounds comprising a polar multiple bond as defined above can be selected from the group consisting of carbon dioxide, aldehydes, ketones, carboxylic acid halides, esters, imines, thioaldehydes, thioketones and thioesters. Compounds with an activated hydrogen are for example carboxylic acids or compounds carrying one or more hydroxy, amino, imino or thio groups.

Here and hereinbelow the term "alkyl" represents a linear or branched alkyl group. By using the form "$C_{1-n}$-alkyl" the alkyl group is meant to have 1 to n carbon atoms. $C_{1-6}$-alkyl represents for example methyl, ethyl, propyl, isopropyl, butyl, isobutyl, sec-butyl, tert-butyl, pentyl and hexyl. An "alkyl" group $R^1$ in formula I may carry one or more additional —MgX groups.

Here and hereinbelow the term "cycloalkyl" represents a cycloaliphatic group having 3 carbon atoms or more. Cycloalkyl represents mono- and polycyclic ring systems such as cyclopentyl, cyclohexyl, cycloheptyl, cyclooctyl, adamantyl or norbornyl. A cycloalkyl group $R^1$ in formula I may carry one or more additional —MgX groups.

Here and hereinbelow the term "alkenyl" represents a linear or branched radical bearing a C=C double bond, optionally substituted with one or more halogen atoms and/or optionally substituted $C_{1-6}$-alkyl, $C_{1-6}$-alkoxy or di-$C_{1-6}$-alkylamino groups. Examples are ethenyl, 1-propenyl, 1-butenyl, or isopropenyl. An alkenyl group $R^1$ in formula I may carry one or more additional —MgX groups.

Here and hereinbelow the term "alkynyl" represents a linear or branched radical bearing a C≡C triple bond, optionally substituted with one or more halogen atoms and/or optionally substituted $C_{1-6}$-alkoxy or di-$C_{1-6}$-alkylamino groups. Examples are ethynyl, 1-propynyl, 1-butynyl, 1-pentynyl. An alkynyl group $R^1$ in formula I may carry one or more additional —MgX groups.

Here and hereinbelow the term "aryl" represents an aromatic group, preferably phenyl or naphthyl optionally being further substituted with one or more halogen atoms and/or optionally substituted $C_{1-6}$-alkyl, $C_{1-6}$-alkoxy or di-$C_{1-6}$-alkylamino groups. An aryl group $R^1$ in formula I may carry one or more additional —MgX groups.

Here and hereinbelow the term "aralkyl", represents an $C_{1-8}$ alkyl group as defined above, substituted with an aryl or hetaryl moiety selected from the group consisting of phenyl, naphthyl, furanyl, thienyl, benzo[b]furanyl, benzo[b]thienyl, said aryl or hetaryl moiety optionally being substituted with one or more halogen atoms, amino groups, and/or optionally substituted $C_{1-6}$ alkyl, $C_{1-6}$ alkoxy or di-$C_{1-6}$-alkylamino groups. An aralkyl group $R^1$ in formula I may carry one or more additional —MgX groups.

Here and hereinbelow the term "alkoxy" represents a linear or branched alkoxy group. By using the form "$C_{1-n}$-alkoxy" the alkyl group is meant having 1 to n carbon atoms. $C_{1-6}$-alkoxy represents for example methoxy, ethoxy, propoxy, isopropoxy, butoxy, isobutoxy, sec-butoxy, tert-butoxy, pentyloxy and hexyloxy.

Here and hereinbelow the term "cycloalkoxy" represents a cycloalkoxy group having 3 carbon atoms or more. Cycloalkyl represents for example cyclopentyloxy, cyclohexyloxy, cycloheptyloxy, cyclooctyloxy or cyclodecyloxy.

Here and hereinbelow the term "di-$C_{1-6}$-alkylamino" represents a dialkylamino group comprising two alkyl moieties independently having 1 to 6 carbon atoms. Di-$C_{1-6}$-alkylamino represents for example N,N-dimethylamino, N,N-diethylamino, N-ethyl-N-methylamino, N-methyl-N-propylamino, N-ethyl-N-hexylamino or N,N-dihexylamino.

Often the primary reaction product of a Grignard type reaction is an intermediate which carries for example a —O—MgX or —S—MgX group. Said intermediate is converted to give the desired reaction product after solvolysis, such as hydrolysis.

Reactions (i) to (xviii) depict preferred embodiments of Grignard reactions and reaction sequences to be performed in a multi-injection microreactor according to the present method.
(i) By reacting a Grignard reagent of formula I or II, wherein $R^1$ and X are as defined above with a compound of formula

    (III), wherein $R^2$ is as defined above and X is halogen, wherein the halogen in compounds of formula I and III may be the same of different,
compounds of formula

    (IV), wherein $R^1$ and $R^2$ are as defined above, are obtained.
(ii) By reacting a Grignard reagent of formula I or II, wherein $R^1$ and X are as defined above with
(a) formaldehyde, or
(b) an aldehyde of formula

    (V), wherein $R^2$ is selected from the group consisting of alkyl, cycloalkyl, alkenyl, alkynyl, aryl and aralkyl, or
(c) a ketone of formula

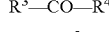    (VI), wherein $R^3$ and $R^4$ are the same or different and are selected from the group consisting of alkyl, cycloalkyl, alkenyl, alkynyl, aryl and aralkyl, primary, secondary and tertiary alcohols of formulae (a) $R^1$—$CH_2$—OH (VII), (b) $R^1$—CHOH—$R^2$ (VIII), and (c) $R^1$—$CR^3R^4$—OH (IX), respectively, wherein $R^1$, $R^2$, $R^3$ and $R^4$ are as defined above, are obtained.
(iii) By reacting a Grignard reagent of formula I or II, wherein $R^1$ and X are as defined above with carbon dioxide leads to the formation of carboxylic acids of formula $R^1$—COOH (X), wherein $R^1$ is as defined above.
(iv) By reacting a Grignard reagent of formula I or II, wherein $R^1$ and X are as defined above with a acetyl halide of formula $R^2$—COX (XI), wherein $R^2$ is as defined above, and wherein X is chlorine, bromine or iodine,
a ketone of formula $R^1$—CO—$R^2$ (XII), wherein $R^1$ and $R^2$ are as defined above, is obtained.
(v) By reacting a Grignard reagent of formula I or II, wherein $R^1$ and X are as defined above with a formate of formula

HCOO$R^2$ (XIII), wherein $R^2$ is as defined above,
depending on the reaction conditions
(a) an aldehyde of formula $R^1$—CHO, wherein $R^1$ is as defined above, or
(b) a secondary alcohol of formula $R^1$—CHOH—$R^2$ VIII, is obtained.
(vi) By reacting a Grignard reagent of formula I or II, wherein $R^1$ and X are as defined above with a carboxylate of formula $R^2$—COO$R^3$ (XIV), wherein $R^2$ and $R^3$ is as defined above,
depending on the reaction conditions
(a) a ketone of formula $R^1$—CO—$R^2$ (XII), wherein $R^1$ and $R^2$ are as defined above, or
(b) a tertiary alcohol of the formula $R^1$—C($R^2$)$_2$—OH (XV)

wherein $R^1$ and $R^2$ are as defined above,
is obtained.
In a preferred embodiment the method is useful for the preparation of triphenylmethanol from ethyl benzoate and phenylmagnesium bromide
(vii) By reacting a Grignard reagent of formula I or II, wherein $R^1$ and X are as defined above with a nitrile of formula $R^2$—CN (XVI), wherein $R^2$ is as defined above, a compound of formula $R^1$—CO—$R^2$ (XII), wherein $R^1$ and $R^2$ are as defined above, is obtained.

(viii) By reacting a Grignard reagent of formula I or II, wherein $R^1$ and X are as defined above with an imine, of formula $(R^2)_2C$=$NR^3$ (XVII), wherein $R^2$ and $R^3$ are as defined above, a compound of formula $R^1(R^2)_2C$—$NHR^3$ (XII), wherein $R^1$, $R^2$ and $R^3$ are as defined above, is obtained.
(ix) By reacting a Grignard reagent of formula I or II, wherein $R^1$ and X are as defined above with deuterium oxide, a compound of formula $R^1$-D (XVIII), wherein $R^1$ is as defined above, is obtained.
(x) By reacting a Grignard reagent of formula I or II, wherein $R^1$ and X are as defined above with sulfur, a compound of formula $R^1$—SH (XIX), wherein $R^1$ is as defined above, is obtained.
(xi) By reacting a Grignard reagent of formula I or II, wherein $R^1$ and X are as defined above with ethylene oxide, a compound of formula $R^1$—$(CH_2)_2$—OH (XX), wherein $R^1$ is as defined above, is obtained.
(xii) By reacting a Grignard reagent of formula I or II, wherein $R^1$ and X are as defined above with thionyl chloride, a compound of formula $(R^1)_2S$=O (XXI), wherein $R^1$ is as defined above, is obtained.
(xiii) By reacting a Grignard reagent of formula I or II, wherein $R^1$ and X are as defined above with
(a) a phosphoryl halide, or
(b) a phosphonic acid dihalide of formula $R^2$—PO$X_2$ (XXII), wherein $R^2$ and X is as defined above, or
(c) a phosphinic acid halide of formula $R^2R^3$POX (XXIII), wherein $R^2$ and $R^3$ are the same or different and are as defined above, and wherein X is as defined above,
by substitution of the halides, phosphine oxides of formulae (a) $(R^1)_3$PO (XXIV), (b) $(R^1)_2R^2$PO (XXV), and (c) $R^1R^2R^3$PO (XXVI), respectively, wherein $R^1$, $R^2$ and $R^3$ are as defined above, are obtained.
The method is particularly important for the preparation of trioctylphosphine oxide.
(xiv) Mixed phosphine oxides can be obtained in a two stage process by firstly reacting Grignard reagent of formula I or II, wherein $R^1$ and X are as defined above with a secondary phosphite of formula $(R^2O)_2$PHO (XXVII), wherein $R^1$ is as defined above, to give a compound of formula $(R^1)_2$POMgX (XXVIII), wherein R¹ and X are as defined above, and
secondly reacting the compound of formula XXVIII with a compound of formula

R²—X     (III), wherein R² and X is as defined above, to obtain a compound of formula (R¹)₂R²PO     (XXV), wherein R¹ and R² are as defined above.

In a preferred embodiment of reaction sequence (xiv) the feed of the compound of formula III in the second step may be performed (a) outside the microreactor, (b) in a second microreactor or (c) in the same microreactor as the first reaction, the latter in at least one "next" injection point after formation of the compound of formula XXVIII.

(xv) By reacting a Grignard reagent of formula I or II, wherein R¹ and X are as defined above with a compound of formula

R²—SiX₃     (XXIX), wherein R² and X are as defined above, compounds of formula R¹R²SiX₂     (XXX), (R¹)₂R²SiX     (XXXI), and (R¹)₃R²Si     (XXXII), wherein R¹, R² and X are as defined above, are obtained.

When carrying out the reaction to reach completion compounds of formula XXXII will be the main product. The method is especially suitable for arylmagnesium halides, preferably arylmagnesium bromides.

(xvi) By reacting a Grignard reagent of formula I or II, wherein R¹ and X are as defined above with compound MX$_m$, wherein M is selected from the group consisting of a metal from groups 3 to 15 of the periodic table including boron, and wherein X is as defined above and m is an integer from 3 to 5 and corresponds to the valence of the metal M, a compound of formula X$_{m-n}$M(R¹)$_n$     (XXXIII), wherein M, R¹ and m are as defined above, and wherein n corresponds to the amount of exchanged halogen atoms X, or optionally after hydrolysis a compound of formula (HO)$_{m-n}$M(R¹)$_n$     (XXXIV)

wherein M, R¹, m and n are as defined above, are obtained.

(xvii) By reacting a Grignard reagent of formula I or II, wherein R¹ and X are as defined above with a compound of formula

R¹—C≡C—H     (XXXV), wherein R¹ is as defined above, a further Grignard reagent of formula R¹—C≡C—Mg—X     (XXXVI), wherein R¹ and X are as defined above, is obtained.

(xviii) By reacting a Grignard reagent of formula

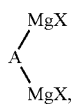
     (XXXVII)

wherein X is as defined above, A is a group —(CH₂)$_n$—, and n is an integer equal to or greater than 3, or a group —CH₂—B—CH₂— with B being a carbocyclic ring of 5 to 7 ring carbon atoms, with a compound of formula L$_m$MX₂     (XXXVIII), wherein L is a ligand selected from the group consisting of 1,5-cyclooctadiene, carbon-monoxide, and arenes like benzene, p-cymene or pentadienyl, wherein m is an integer equal to or greater than 1, a compound of formula

     (XXXIX)

wherein M, L, A and m are as defined above, is obtained.

In a preferred embodiment of reaction scheme xviii) in compounds of formulae XXXVII and XXXIX, A is a carbocyclic ring like

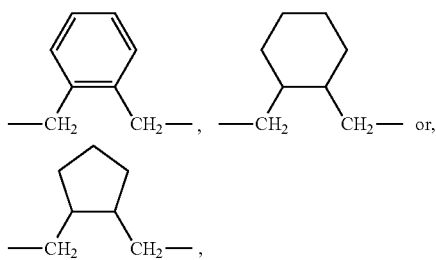

wherein each ring may contain one or more further substitutents such as alkyl or alkoxy groups. Thus in a further preferred embodiment of reaction scheme (xviii), (η⁵-C₅H₅)₂MCl₂ is reacted with

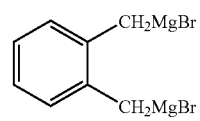

to give a metallacyclus of formula

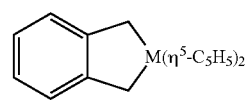

wherein M is Ti, Zr, Hf, Nb.

Figure 2:
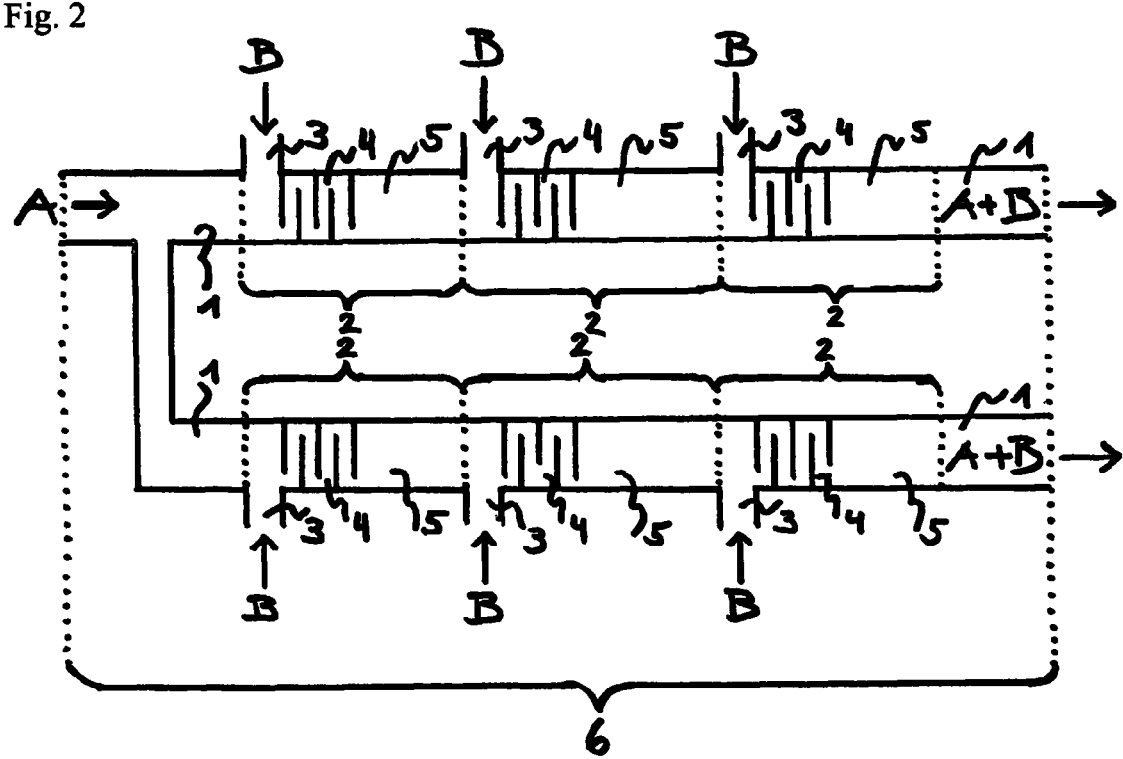
FIG. 2 illustrates a second embodiment of the microreactor of the present invention and shows two flow paths each having three injection points.

FIG. 1 and FIG. 2 show two examples of feeding a flow B at various injection points to a flow A. The microreactor (6) in FIG. 1 comprises one flow path with three injection points, the microreactor (6) in FIG. 2 comprises two flow paths each having three injection points. There may be more than two flow paths present, as well as more than three injection points in each flow path. Thus, the 2$^{nd}$ reactant may be fed at the injections points to a first flow generated by the fluid comprising the 1$^{st}$ reactant. From an economical point of view the more expensive and/or more reactive reactant is advantageously fed to the first flow comprising the cheaper and/or less reactive reactant. In most cases the Grignard reagent will be the more expensive and/or more reactive reactant.

Furthermore, there are no structural limits regarding the injection points, the mixing zones and/or the reaction zones. Only for the reason of better understanding of the parts of the microreactor used in the present invention the microreactors in FIG. 1 and FIG. 2 are depicted as a linear strung-out hollow space. Nevertheless, the flow path(s) (1) may be tortuously bent as known in the art. Furthermore, different mixing zones and/or reaction zones need not have the same dimensions in width or length. It is further not necessary to use a microreactor which contains all of the features mentioned above in one physical entity. It is also possible to externally connect additional injection points, mixing zones, reaction zones, each optionally cooled or heated, to a flow path.

Feeding only a fraction of the amount necessary to reach completion of the Grignard reaction while using more than one injection point leads to an increase the number of hot spots in the microreactor while the temperature rise in each hot spot is reduced as compared to typical microreactors with only one mixing and reaction zone. In addition, since one of the two compounds is diluted in the first flow comprising the other compound, formation of side products is reduced and yields are increased. Thus, the inventive method provides an improved control over reactions.

In the present invention each of the at least two fluids independently can be a liquid, a gas or a supercritical fluid. Depending on the mixing properties of the mixing zone it is not necessary that the at least two fluids are completely miscible.

In addition to the at least one general flow path, at least one injection point, at least one mixing zone and at least one reaction zone a suitable microreactor for the inventive method may comprise additional structural elements such as temperature adjustable retention volumes, temperature adjustable premixing volumes and others known in the art.

It has been found that using a microreactor is particularly advantageous for Grignard type reactions if used with multiple-injection points. According to the present method, improved control over a fluid Grignard type reaction can be achieved, which can result in significant improvements in reaction product yield and/or purity, as well as other benefits. The reaction starts after contacting the reactive fluids A and B in the mixing zone (3) and continues in a reaction zone (3). In a preferred embodiment the flow path(s) (1) has/have a width in the range of 10 to 10000 micrometers and a cross section of 0.1 square centimeters or less. More preferably the flow path width is in a range of 10 to 500 micrometers, or even more preferably in a range of 10 to 200 micrometers.

In a further preferred embodiment heat or cooling independently is supplied to the reservoirs of reactants, injection point(s) (3), the mixing zone(s) (4) and/or the reaction zone(s) (5) or any other structural entity of the microreactor used. Preferably the heat or cooling is supplied by an external source. Said heat or cooling can be supplied to initiate, maintain and/or slow down the reaction. Preferably heat is supplied to initiate and/or maintain the reaction, whereas cooling is supplied to slow down the reaction. In rare cases heat may be supplied to slow down the reaction, whereas cooling may be supplied to initiate and/or maintain the reaction.

In case of fast reactions which essentially take place in the mixing zone the reaction zone can be used to adjust the temperature of the reaction mixture before injecting the next fraction of the compound to react in a Grignard type reaction with the compound already present in the first flow.

Generally, the first flow (1) of fluids containing the reaction product is quenched after being discharged from the microreactor. Fast exothermic reactions which are almost completed when the reaction mixture has passed the mixing zone may require additional cooling while passing the reaction zone to suppress side product formation. Performing slow reactions to complete conversion often leads to side products. In a preferred embodiment the product is isolated after quenching the reaction. In case the reaction does not reach completion in the mixing zone for several Grignard reactions it may be suitable to feed the discharged first flow from the reaction zone or the microreactor into an external retention volume for further reaction, for other Grignard reactions it may be suitable after the last injection point to quench the first flow directly after being discharged from the reaction zone or from the microreactor before it reaches completion to avoid overreaction.

We have shown in the examples below that in Grignard reactions the yield increases with the number of injection points. Comparing the benefit of each additional injection zone with the efforts and drawbacks of connecting or building a further injection zone (new microreactor design, in general increase of required hardware, additional programming work, increased fluid pressure, increased danger of leakage) it has been found, that the inventive method is advantageously carried out with a microreactor comprising not more than 7 reaction regions (injection points, mixing zones, reaction zones), preferably 3 to 6 reaction regions.

Glycol ethers, preferably bis(2-methoxyethyl)ether (diglyme) and 1,2-dimethoxyethane (monoglyme, DME), are preferred solvents for carrying out the instant Grignard reactions in microreactors. Especially at low temperatures of 0° C. or lower, Grignard reagents tend to flocculate, coagulate or even crystallize and thus plug the microstructures. It could be shown that carrying out Grignard reactions in microreactors in the presence of at least one glycol ether prevents flocculation, coagulation or crystallization of Grignard reagents and thus plugging of the microstructures (channels, micromixer, internal flow path(s)), especially at low temperatures. It could be shown that (under identical conditions) Grignard solutions comprising at least one glycol ether have an extended storage life time as compared to Grignard solutions without glycol ethers. Furthermore, such Grignard solutions may contain up to about 20 wt-% of the Grignard reagent or more while stored and/or fed to the microreactor at a temperature of about 0° C. or less, preferably at about −5° C. or less, even more preferred at about −15° C. or less. In a further preferred embodiment the Grignard reagent is solved in a mixture comprising between 10 and 50 wt.-% of at least one glycol ether, more preferably between 20 and 40 wt-%, even more preferred about 30 wt-%. In another preferred further embodiment the glycol ether is bis(2-methoxyethyl)ether and/or 1,2-dimethoxyethane. Other suitable solvents which can be used in the present method are anhydrous diethyl ether and/or tetrahydrofuran.

Further objects, advantages and features may be derived from the depending claims and the described embodiments of the present invention.

DESCRIPTION OF THE DRAWINGS

FIG. 1 is a schematic drawing of a microreactor (6) comprising a flow path (1) through the whole microreactor and embedded three reaction regions (2) each, reaction region comprising an injection point (3), a mixing zone (4) and a reaction zone (5), wherein a fluid B is fed to a fluid A.

FIG. 2 shows a schematic drawing of a microreactor comprising two such flow paths.

EXAMPLES

The microreactors used in the examples and comparison example were made of different materials (glass or metal) and differently built systems. Some were integrated microreactor entities wherein injection point(s), mixing zone(s) and reaction zone(s) are built in one physical entity. Others are made from single elements (injection point(s), mixing zone(s) and reaction zone(s)) which are connected via external fittings. Some microreactors were temperature adjusted by immersing in a temperature controlled bath without having any additional elaborated temperature adjustment systems in place. Others also contained an efficient internal temperature adjustment system wherein a temperature controlled fluid is fed to the outside surface of injection point(s), mixing zone(s) and reaction zone(s) to provide an efficient and quick temperature adjustment. To facilitate the evaluation of the influence of the number of injection points in all examples the Grignard reagent ($2^{nd}$ reactant) was fed to a $1^{st}$ reactant in a proportional way corresponding to the number of inlet points. With two, three, four, five or six inlet points about 50, 33.3, 25, 20 or 16.6 mol-% of the $2^{nd}$ reactant necessary to reach completion of the reaction respectively are fed at each inlet point. Normally the effluent of the microreactor (comprising the product) has been quenched and collected. In most cases the effluent has been quenched with HCl.

Example 1

In two self assembled multi-injection microreactors having 2 to 6 reaction regions assembled from separate injection points, mixing zones and reaction zones (each reaction comprising one injection point, one mixing zone and one reaction zone), 2-chloro propionic chloride (13.5 wt %) in tetrahydrofuran (THF, 86.5 wt %) as flow A and phenethylmagnesium bromide (1 eq., 10 wt %) in THF (1 eq., 90 wt %) as flow B were reacted. The microreactors were placed in a bath at 20° C. Temperature adjustment of the microreactors depended on heat exchange on the outer surface of the single parts of the modules. The microreactor of examples 1.1 to 1.5 comprised reaction zones of about 0.2 mL internal volume allowing almost no cooling between the injection points. The microreactor of examples 1.6 to 1.10 comprised reaction zones of about 2.0 mL internal volume allowing at least a low effective cooling (LEC) between the injection points. Flow rates of 20 and 40 g/min were performed. The $2^{nd}$ reactant was fed to the $1^{st}$ reactant in equimolar ratio. The yields of the product 4-chloro-1-phenyl-pentan-3-one collected after the respective reaction zone are shown in table 1 and 2 in relation to feed rate and cooling conditions.

Comparison Example 1

In a single-injection microreactor equipped with one injection point, one mixing zone and one reaction zone, the reactants of example 1 were reacted with and without cooling. Flow rates of 20 and 40 g/min were performed. Flow B (Grignard reagent) was fed to flow A ($1^{st}$ reactant) in such a way that in the mixing zone both reactants were present in equimolar ratio. The yields of the product 4-chloro-1-phenyl-pentan-3-one being collected after the respective reaction zone and quenched are shown in table 1 in relation to feed rate and cooling conditions.

Example 2

In two multi-injection microreactors having 4 reaction regions (each comprising one injection point, one mixing zone and one reaction zone of 1.08 mL internal reaction volume), 2-chloro propionic chloride (13.5 wt %) in tetrahydrofuran (THF, 86.5 wt %) as flow A and phenethyl-magnesium bromide (1 eq., 10 wt %) in THF (1 eq., 90 wt %) as flow B were reacted. Micro-reactor MR1 comprised internal heat exchange structures and provided a very efficient cooling (VEC) while temperature adjustment of metal microreactor MR2 was performed by submersing the microreactor in a temperature adjusted bath and provided only a low efficient cooling (LEC) between the injection points. The temperatures were displayed in table 3. Total flow rates of 20 and 40 g/min after last injection were performed. The $2^{nd}$ reactant (flow B) is fed to the first reactant in a proportion corresponding to the number of inlet points. About 25 mol-% of flow B necessary to reach completion of the reaction respectively were fed at each inlet point to the first flow. After the last injection the reagents of flow B and flow A were fed in equimolar amount. The yields of the product 4-chloro-1-phenyl-pentan-3-one being collected after the respective reaction zone and quenched are shown in table 2 in relation to feed rate and cooling conditions.

Example 3

The reaction of example 1 has been performed in two different microreactors with a flow of 18 g/min. MR2 is a metal microreactor submersed in a cooling bath without further cooling facilities (LEC), MR3 is a glass microreactor with an active cooling system with internal heat exchange structures similar to MR1 providing a very efficient cooling (VEC). The yields obtained with microreactors having two injection points at −20, 0 and 20° C. respectively (Examples 3.1 and 3.3), or three injection points at −20, 0 and 20° C. respectively (Examples 3.2 and 3.4) are collected in table 4.

Comparison Example 2

The yields of the reaction of example 1 performed under the conditions of example 3 with microreactors having one injection point (Comparison Examples 2.1 and 2.2), are collected in table 4.

Example 4

In a commercially available multiple injection microreactor from Corning (each reaction comprising one injection point, one mixing zone and one reaction zone) dimethyl oxalate (10, or 20 wt % respectively) in bis(2-methoxyethyl)ether (ad 100 wt %) as flow A and ethyl-magnesium chloride (19.1 wt %) in a mixture of bis(2-methoxyethyl)ether (30 wt %) and tetrahydrofuran (THF, ad 100 wt %) as flow B were reacted. HCl in a HCl/Mg molar ratio of about 1.15 has been used to quench the reaction in the microreactor effluent. Table 5 displays the respective dimethyl oxalate content in flow A [wt.-%], the Grignard/oxalate stoichiometry [mol/mol], the total flow [g/min], the temperature of the heat reservoir used for thermal adjustment of the microreactor, as well as yield (Y, [%]) of product (2-MOB=methyl 2-oxo-butyrate), conversion (C, [%]) and selectivity (S, [%]).

Comparison Example 3

In a commercially available mono injection NIM microreactor from Corning dimethyl oxalate (10, 15 or 20 wt % respectively) in bis(2-methoxyethyl)ether (ad 100 wt %) as flow A and ethylmagnesium chloride (19.1 wt %) in a mixture of bis(2-methoxyethyl)ether (30 wt %) and tetrahydrofuran (THF, ad 100 wt %) as flow B were reacted. HCl in a HCl/Mg molar ratio of about 1.15 has been used to quench the reaction in the microreactor effluent. Table 6 displays the respective dimethyl oxalate content in flow A [wt.-%], the Grignard/oxalate stoichiometry [mol/mol], the total flow [g/min], the temperature of the heat reservoir used for thermal adjustment of the microreactor, as well as yield (Y, [%]) of product (2-MOB=methyl 2-oxo-butyrate), conversion (C, [%]) and selectivity (S, [%]).

TABLE 1

|  | Comparison example 1, 1 injection point | Example 1.1, 2 injection points | Example 1.2, 3 injection points | Example 1.3, 4 injection points | Example 1.4, 5 injection points | Example 1.5, 6 injection points |
| --- | --- | --- | --- | --- | --- | --- |
| 40 g/min, no cooling | 22.5% | 27.0% | n.a. | 30.0% | 31.0% | 33.0% |
| 20 g/min, no cooling | 21.5% | 26.7% | 31.0% | 32.7% | 35.0% | 36.0% | n.a. = not available; LEC = "low efficient cooling"; VEC = "very efficient cooling"

TABLE 2

|  | Comparison example 1, 1 injection point | Example 1.6, 2 injection points | Example 1.7, 3 injection points | Example 1.8, 4 injection points | Example 1.9, 5 injection points | Example 1.10, 6 injection points |
| --- | --- | --- | --- | --- | --- | --- |
| 40 g/min, LEC | 22.5% | 29.5% | 33.5% | n.a. | 37.5% | 37.5% |
| 20 g/min, LEC | 21.5% | 29.0% | 33.5% | 36.3% | 37.5% | 38.5% | n.a. = not available; LEC = "low efficient cooling"; VEC = "very efficient cooling"

TABLE 3

|  | Example 2.1, MR1, 0° C., VEC | Example 2.2, MR1, 20° C., VEC | Example 2.3, MR2, 20° C., LEC |
| --- | --- | --- | --- |
| 10 g/min | n.a. | n.a. | n.a. |
| 20 g/min | n.a. | n.a. | 36.3% |
| 38 g/min | n.a. | n.a. | 35.0% |
| 40 g/min | 46.3% | 40.7% | n.a. |
| 60 g/min | 43.5% | 37.1% | n.a. |
| 80 g/min | 42.3% | 35.9% | n.a. |
| 100 g/min | 40.1% | 33.7% | n.a. | n.a. = not available; LEC = "low efficient cooling"; VEC = "very efficient cooling"

TABLE 4

|  | −20° C. | 0° C. | 20° C. |
| --- | --- | --- | --- |
| Comparison example 2.1, MR2, LEC | 29.8% | 25.6% | 21.6% |
| Example 3.1, MR2, LEC | n.a. | 32.5% | 28.1% |
| Example 3.2, MR2, LEC | n.a. | 36.7% | 30.0% |
| Comparison example 2.2, MR3, VEC | 36.1% | 30.6% | 22.8% |
| Example 3.3, MR3, VEC | n.a. | 36.7% | 30.0% |
| Example 3.4, MR3, VEC | n.a. | 30.0% | 32.9% | n.a. = not available; LEC = "low efficient cooling"; VEC = "very efficient cooling"

TABLE 5

| Ex. # | Feed-1 [wt.-%] | Stoichiometry [mol/mol] | Flow [g/min] | T [° C.] | Y [%] | C [%] | S [%] |
| --- | --- | --- | --- | --- | --- | --- | --- |
| 4.1 | 10.0 | 1.17 | 39.9 | −5 | 84.6 | 98.9 | 85.6 |
| 4.2 | 10.0 | 1.17 | 40.0 | −15 | 89.2 | 100.0 | 89.2 |
| 4.3 | 15.0 | 1.15 | 39.9 | −5 | 81.7 | 97.8 | 83.5 |
| 4.4 | 15.0 | 1.11 | 40.0 | −15 | 87.4 | 98.4 | 88.9 |
| 4.5 | 20.0 | 1.14 | 39.9 | −5 | 78.0 | 98.2 | 79.4 |
| 4.6 | 20.0 | 1.16 | 40.0 | 5 | 84.7 | 99.0 | 85.5 |
| 4.7 | 20.0 | 1.07 | 40.0 | 5 | 70.9 | 92.6 | 76.5 |
| 4.8 | 20.0 | 1.11 | 40.0 | −5 | 77.6 | 95.6 | 81.2 |
| 4.9 | 20.0 | 1.05 | 40.0 | −15 | 82.7 | 95.0 | 87.1 |

TABLE 6

| C.-Ex. # | Feed-1 [wt.-%] | Stoichiometry [mol/mol] | Flow [g/min] | T [° C.] | Y [%] | C [%] | S [%] |
| --- | --- | --- | --- | --- | --- | --- | --- |
| 3.1 | 10.0 | 1.17 | 40.2 | −15 | 81.6 | 96.1 | 84.9 |
| 3.2 | 10.0 | 1.16 | 40.1 | −5 | 77.3 | 94.8 | 81.5 |
| 3.3 | 10.0 | 1.17 | 40.0 | 5 | 73.4 | 94.4 | 77.7 |
| 3.4 | 15.0 | 1.17 | 39.9 | −5 | 67.7 | 94.9 | 71.3 |
| 3.5 | 15.0 | 1.17 | 40.0 | −15 | 74.0 | 96.6 | 76.6 |
| 3.6 | 20.0 | 1.23 | 38.7 | −5 | 53.3 | 90.9 | 58.6 |

The invention claimed is:

1. A method for carrying out a Grignard reaction comprising mixing at least two fluids, one of the at least two fluids comprising a compound ($1^{st}$ reactant) able to react with a Grignard reagent in a Grignard type reaction, and another fluid comprising the Grignard reagent ($2^{nd}$ reactant), and optionally further fluids, said mixing taking place in a microreactor comprising at least one flow path for one of the at least two fluids comprising either the $1^{st}$ or $2^{nd}$ reactant, said flow path(s) comprising at least two reaction regions, each reaction region comprising an injection point for feeding the other one of the two fluids comprising either the $2^{nd}$ or $1^{st}$ reactant with the proviso that the reactant in the at least one flow path and the reactant in the injection point are not the same, a mixing zone in which the at least two fluids contact each other and a reaction zone, and wherein the microreactor optionally provides one or more additional residence time volumes, and wherein in said method one of the at least two fluids comprising either the $1^{st}$ or $2^{nd}$ reactant establishes a first flow and wherein the other one of the at least two fluids comprising either the $2^{nd}$ or $1^{st}$ reactant is injected into said first flow at least at two injection points along said flow path(s) in a way such that at each injection point only a fraction of the amount necessary to reach completion of the Grignard type reaction is injected.

2. The method of claim 1, wherein the flow path(s) has/have a width in the range of 10 to 10000 micrometers and a cross section of 0.1 square centimeters or less.

3. The method of claim 2, wherein the flow path width is in a range of 10 to 500 micrometers.

4. The method of claim 3, wherein the flow path width is in a range of 10 to 200 micrometers.

5. The method of claim 1 further comprising supplying heating or cooling independently to the injection point(s), the mixing zone(s) and/or the reaction zone(s).

6. The method of claim 5, wherein heat or cooling is supplied to initiate, maintain and/or slow down the reaction.

7. The method of claim 6, wherein heat is supplied to initiate and/or maintain the reaction.

8. The method of claim 6, wherein cooling is supplied to slow down the reaction.

9. The method of claim 1, wherein the flow path(s) of the microreactor comprises 3 to 6 reaction regions.

10. The method of claim 1, wherein, when the reaction between the $1^{st}$ and $2^{nd}$ reactants is a slow reaction, the reaction is quenched after the last reaction zone before it reaches completion.

11. The method of claim 1, wherein the Grignard reagent ($2^{nd}$ reactant) is a compound of formula.

$$R^1-Mg-X \qquad (I),$$

or $$R^1-Mg-R^2 \qquad (II),$$

wherein $R^1$ is selected from the group consisting of alkyl, cycloalkyl, alkenyl, alkynyl, aryl and aralkyl, and wherein X is selected from the group consisting of chlorine, bromine and iodine.

12. The method of claim 1, wherein the $1^{st}$ reactant is a compound of formula $$R^2-X \qquad (III),$$

wherein $R^2$ is selected from the group consisting of alkyl, cycloalkyl, alkenyl, alkynyl, aryl and aralkyl, and X is selected from the group consisting of chlorine, bromine and iodine.

13. The method of claim 1, wherein the $1^{st}$ reactant is a compound comprising one or more polar multiple bonds like C=O, C=N, C≡N, C=S, N=O and S=O.

14. The method of claim 13, wherein the $1^{st}$ reactant is selected from a group consisting of carbon dioxide, aldehydes, ketones, carboxylic acid halides, esters, imines, thioaldehydes, thioketones and thioesters.

15. The method of claim 1, wherein the $1^{st}$ reactant is a compound having at least one activated hydrogen atom.

16. The method of claim 15, wherein the $1^{st}$ reactant is selected from a group consisting of carboxylic acids and compounds carrying one or more hydroxy, amino, imino or thio groups.

17. A method for carrying out a Grignard reaction in a microreactor comprising:
establishing at least one flow path of a first fluid through the microreactor, the first fluid comprising a $1^{st}$ reactant and the flow path comprising at least two reaction regions, each reaction region comprising an injection point, a mixing zone and a reaction zone
injecting and mixing a second fluid comprising a $2^{nd}$ reactant into the at least one flow path through the injection points in the at least two reaction regions to form a reaction mixture;
controlling the residence time of the reaction mixture in the microreactor; and
removing the reaction mixture from the microreactor,
wherein at least one of the $1^{st}$ reactant and $2^{nd}$ reactant is a compound able to react with a Grignard reagent in a Grignard type reaction, and at least one of the $1^{st}$ and $2^{nd}$ reactants is the Grignard reagent, with the proviso that neither the $1^{st}$ nor $2^{nd}$ reactants comprises both, wherein at each injection point only a fraction of the amount of the $2^{nd}$ reactant necessary to reach completion of the Grignard type reaction is injected, and wherein the reaction mixture comprises at least one glycol ether.

18. A method for carrying out a Grignard reaction according to claim 1 in a microreactor wherein the reaction mixture comprises at least one glycol ether.

19. The method of claim 17, wherein 10 and 50 wt.-% of at least one glycol ether is present.

20. The method of claim 17, wherein the glycol ether is bis(2-methoxyethyl)ether and/or 1,2-dimethoxyethane.

21. The method of claim 17, wherein the temperature of the Grignard reagent fed to the microreactor is less than or equal to 0° C.

* * * * *